(12) United States Patent
Greene et al.

(10) Patent No.: US 9,261,952 B2
(45) Date of Patent: Feb. 16, 2016

(54) SHIFTING AND RECHARGING OF EMOTIONAL STATES WITH WORD SEQUENCING

(71) Applicant: SPECTRUM ALLIANCE, LLC, Corona Del Mar, CA (US)

(72) Inventors: Pamela Gail Greene, Corona Del Mar, CA (US); David L. Greene, Corona Del Mar, CA (US); Mary Anne Thomas, Black Mountain, NC (US)

(73) Assignee: Spectrum Alliance, LLC, Corona Del Mar, CA (US)

( * ) Notice: Subject to any disclaimer, the term of this patent is extended or adjusted under 35 U.S.C. 154(b) by 604 days.

(21) Appl. No.: 13/759,801

(22) Filed: Feb. 5, 2013

(65) Prior Publication Data

US 2014/0223363 A1    Aug. 7, 2014

(51) Int. Cl.
*G06F 3/01* (2006.01)
*G06Q 90/00* (2006.01)
(52) U.S. Cl.
CPC . *G06F 3/01* (2013.01); *G06Q 90/00* (2013.01)
(58) Field of Classification Search
CPC   G06F 3/04842; G06F 3/048; G06F 17/30867

USPC .......................................................... 715/810
See application file for complete search history.

(56) References Cited

U.S. PATENT DOCUMENTS

| 7,233,900 B2 * | 6/2007 | Kariya | G10L 13/08 704/258 |
| 8,209,182 B2 * | 6/2012 | Narayanan | G06F 17/2785 704/211 |

\* cited by examiner

*Primary Examiner* — Jeffrey A Gaffin
*Assistant Examiner* — Sabrina Greene
(74) *Attorney, Agent, or Firm* — Stetina Brunda Garred & Brucker

(57) ABSTRACT

The shifting and recharging of an emotional state with word sequencing is disclosed. A selection of a first word sequence set is received from the user. The word sequence set is defined by a mood recharging characteristic value, and includes a plurality of words each with at least one corresponding definition. A first one of the plurality of words in the selected first word sequence set is displayed. Then, a first one of the at least one corresponding definition of the first one of the plurality of words in the first word sequence set is displayed while the first one of the plurality of words remains displayed. The definition remains displayed for a time duration corresponding to a predefined cadence rate value. The user is prompted with a question related to the mood recharging characteristic value and associated with the first word sequence set.

21 Claims, 14 Drawing Sheets

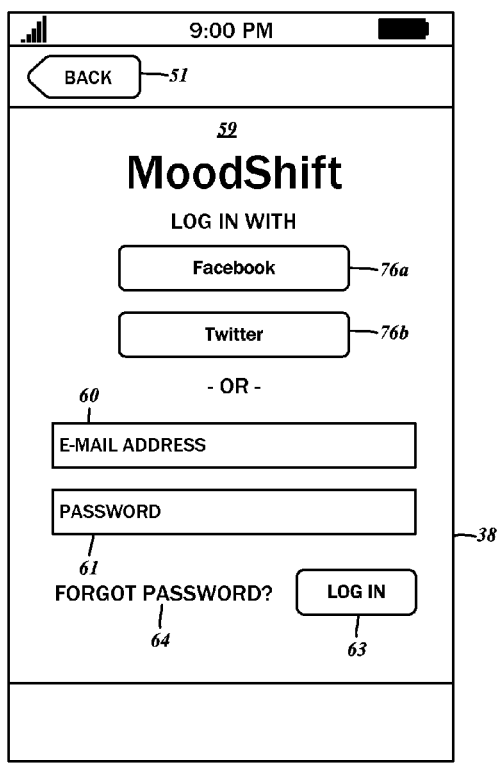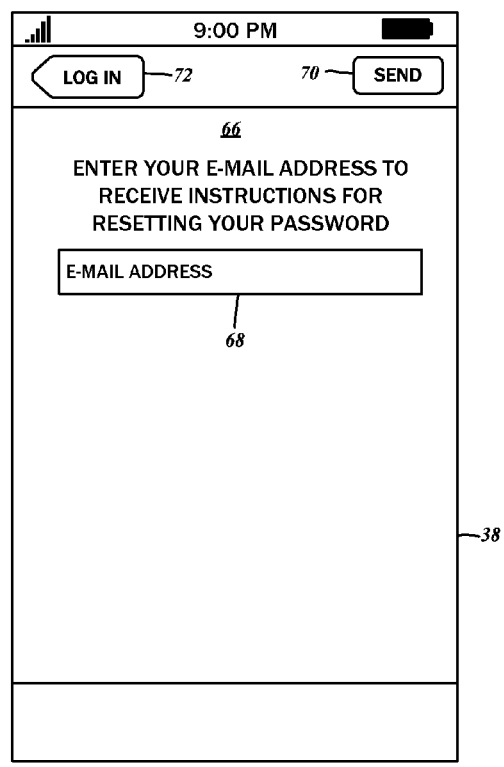
FIG. 2B  FIG. 2C

SHIFTING AND RECHARGING OF EMOTIONAL STATES WITH WORD SEQUENCING

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

The present disclosure relates to mood improvement techniques, and more particularly, to personalized word sequencing methods and systems in accessible devices for shifting and recharging emotional states.

2. Related Art

Contemporary life in all but the most secluded places far from civilization tends to be a chaotic and turbulent experience that places a tremendous amount of stress and anxiety on the individual. Although the harm to emotional well-being that results from major calamities and stressors such as natural disasters, recessions, terrorism, crime, and the like cannot be marginalized, daily demands of the workplace and of the home are significant sources of emotional unrest. For instance, workers are universally under pressure to handle increasing workloads with fewer resources, with ever-decreasing time away from the job to adequately decompress and recharge one's emotions. The problem of occupational stress can be exacerbated by toxic work environments, bullying and harassment, and other inter-personal conflicts with colleagues at various levels. Further, upon leaving work at the end of the day, there may be additional stressors such as family care obligations and tedious household tasks. What should otherwise be a relaxing experience in watching television programs or consuming media such as newspapers and magazines may be agitating and demoralizing at the same time because of all of the negativity expressed therein. Hurtful and egregious comments are not limited to the media, and can come from anyone within an individual's sphere of influence including family, friends, and acquaintances.

What the foregoing amounts to, is a constant, never-ending accumulation of emotional turmoil leading to confusion, disappointment, fear, and unhappiness, the likes of which have a debilitating effect on the homeostasis of humankind. Well understood and documented in the medical literature, emotional unrest induced by acute stressors activates neuronal communications between the heart and the brain. The heart is now considered by many scientists and neurocardiologists to be the primary receptive organ of incoming stressors. The biochemical reactions that follow as a result of incoming stressors may result in the classic "fight or flight" systemic reaction experienced by the body. This reaction causes significant changes in heart rate variability, blood pressure, breathing patterns, hormonal secretions, and sleep patterns affecting every organ system in the body. Acute and chronic emotional unrest suppresses the immune system, rendering an individual more susceptible to common diseases. Examples of unhealthy states associated with emotional unrest are gastrointestinal problems, headache syndromes and assorted back pain syndromes. Significant suppression of the immune system will hinder repair of mutated DNA, which has been linked to the development of cancer.

Aside from the aforementioned somatic effects, emotional unrest is known to be the cause of depression, alcoholism and other substance abuse, and suicide, among many others. It is also known to trigger the onset of schizophrenia, manic episodes, and various psychotic disorders.

Unfortunately, due to the lack of time, energy, and escalating healthcare costs, many individuals suffering under the burdens of emotional unrest neglect to seek assistance. In many cases, the individual is too embarrassed or ashamed due to the instilled belief that one is not mentally strong or resilient enough to deal with the stress, and continues to suffer in silence. To the extent professional help is sought, psychiatry and its related disciplines are increasingly relying upon psychopharmacology to manage emotional unrest. The mechanism-of-action of these drugs is not well understood and is currently being challenged. Problematically, the ineffectiveness of these drugs as reported by researchers, coupled with the serious warnings of possible suicidal and homicidal ideation, raises questions of sustainability.

Accordingly, there is a need in the art for an affordable, mobile, non-drug, rapid delivery modality to impact emotional turmoil. There is a need in the art for systems and methods that target emotional conditions, and are readily accessible for individuals engaged in busy lifestyles.

BRIEF SUMMARY

In accordance with one embodiment of the present disclosure, a method for shifting and recharging an emotional state of a user with word sequencing is contemplated. With the disclosed method, it is possible to "recharge" the user's emotions as a first step toward impacting emotional unrest. The method may be embodied as computer or data-processor-executed instructions that may be run on a mobile device and is therefore readily accessible by the user anywhere. The word sequencing may be presented on a data processing apparatus with a display and an input.

The method may include a step of receiving a selection of a first word sequence set from the user through the input of the data processing apparatus. The word sequence set may be defined by a mood recharging characteristic value. Additionally, the first word sequence set may include a plurality of words each with at least one corresponding definition. The method may continue with generating a first one of the plurality of words in the selected first word sequence set on the display. The first one of the plurality of words may be displayed with a first predefined typeface. The method may also include generating on the display a first one of the at least one corresponding definition of the first one of the plurality of words in the first word sequence set. The definition may be displayed with a second predefined typeface, while the first one of the plurality of words remains generated on the display. The definition may remain displayed for a time duration corresponding to a predefined cadence rate value.

Following these two steps, the method may include prompting the user with a question related to the mood recharging characteristic value. The question may also be associated with the first word sequence set.

The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings:

FIG. 2B is an example user interface showing a login screen;

FIG. 2C is an example user interface showing a password recovery screen;

Common reference numerals are used throughout the drawings and the detailed description to indicate the same elements.

DETAILED DESCRIPTION

The detailed description set forth below in connection with the appended drawings is intended as a description of the presently contemplated embodiments of methods and systems for shifting and recharging an emotional state of a user. This description is not intended to represent the only form in which the disclosed invention may be developed or utilized. The description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

Generally, the methods for shifting and recharging emotional states relies upon word sequencing techniques, in which the user is shown a series of words to affect emotional changes. In particular, the presently contemplated methods target emotions and help "shift and recharge" the user's emotions. While these methodologies are not intended to provide an escape from negative emotion, it is contemplated to utilize such negative emotion as a pathway to its positive counterpart, creating a better mood for the user. Such shifts in mood are immediate, and are envisioned to be sustainable with repeated use.

Figure 1:
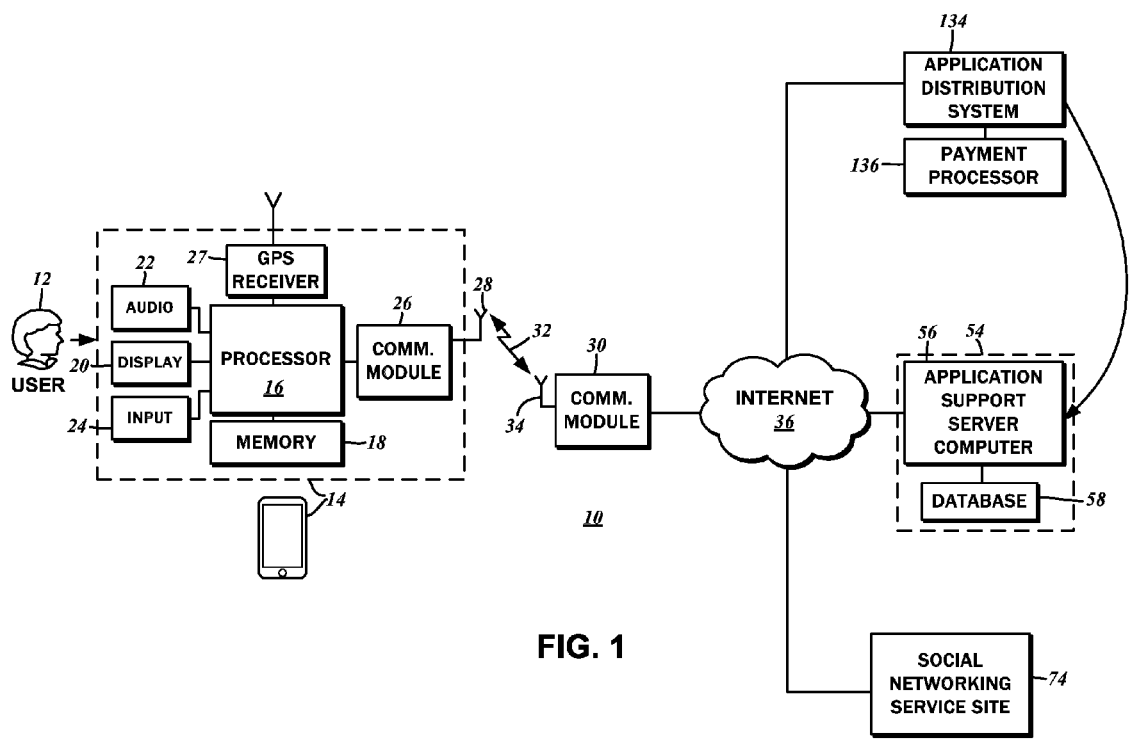
FIG. 1 is a block diagram illustrating an exemplary environment in which various embodiments of the present invention may be implemented, including a data processing apparatus.

With reference to the block diagram of FIG. 1, one exemplary environment 10 in which embodiments of the present disclosure may be implemented is illustrated. As will be described in further detail, much of the interaction for mood shifting and recharging purposes is between a user 12 and a data processing apparatus 14. However, there are peripheral components that play different roles to provide additional functionality. It is contemplated that the data processing apparatus 14 is a mobile data communications device such as a smart phone capable of running software programs, variously referred to in the art as applications, apps, and so forth. Accordingly, at minimum, the data processing apparatus 14 includes a processor 16 that executes a series of preprogrammed instructions that generate certain outputs in response to inputs. These instructions are understood to embody a series of steps that comprise one method for shifting and recharging the emotional state of the user 12. These instructions may be stored in an on-board memory 18 connected to the processor 16.

There are several input and output devices typically included in a mobile data communications device. For instance, there is a display 20 that generates a graphical output from the processor 16. Such outputs are understood to be in response to the execution of the aforementioned preprogrammed instructions. The display 20 is a color liquid crystal display (LCD) device comprised of a plurality of rows and columns of individually activatable pixels.

Since the exemplary data processing apparatus 14 is a smart phone, an audio output device 22 is also contemplated. The audio output device 22 may include a converter that translates a stream of data output by the processor 16 into an audio signal. Additionally, the audio output device 22 may include a transducer that produces sound in response to the audio signal. The execution of the instructions may be invoked or modified via inputs from the user 12 through an input device 24.

Many conventional smart phones utilize a touch screen that is overlaid on the display 20, and taps and other well-known touch inputs at specific locations along the input device 24 corresponding to different positions of graphical user interface elements shown on the display 20 may activate functionality associated therewith. One possible graphical user interface is the virtual keyboard, which is a graphical arrangement of keys for alphanumeric characters, and tapping on a portion of the screen is operative to select or enter that character.

Being a mobile communications device, the data processing apparatus 14 is also understood to include a communications module 26 that is connected to an antenna 28 as well as the processor 16. As will be recognized by those having ordinary skill in the art, the communications module 26 may include an analog/digital converter circuit that, in transmit operations, converts a data stream from the processor 16 to an analog signal. A radio frequency (RF) carrier signal is then applied to the analog signal, amplified, and passed to the antenna 28, which transduces the electrical signal to an electromagnetic radio frequency signal that propagates through the air. The opposite occurs on the receive end with another wireless communications module 30, in which the electromagnetic radio frequency signal 32 passed from an antenna 34 is transduced to an electrical signal and then amplified. The RF carrier signal is removed, and the resulting analog signal is converted to a digital data stream by a digital/analog converter circuit and is passed to another module for further processing. Both of the illustrated wireless communications modules 26, 30 are understood to be capable of bi-directional communications.

In accordance with one embodiment of the present disclosure, through the aforementioned wireless data communications link a connection to the Internet 36 can be established from the data processing apparatus 14. As will be described more fully below, the connection to the Internet 36 is utilized to link the data processing apparatus 14 to various servers also connected to the Internet 36 and provide additional functionality to the presently disclosed method for shifting and recharging the emotional state of the user 12. For these purposes, standard TCP/IP (transmission control protocol/Internet protocol) transport modalities may be used, along with higher level communications utilizing HTTP (Hyper Text Transfer Protocol) as well as any other suitable inter-process communications modality. The wireless data communications link may be of a relatively short distance as would be the case with WiFi/802.11x, or of further distances and greater coverage area as would be the case with cellular data networks. A variety of standards exist, including GSM (Global System for Mobile Communications), WCDMA (Wideband Code Division Multiple Access) and so forth. Any type of wireless communications modality may be utilized to establish the data communications link to the Internet 36, though it is understood that both the wireless communications module 30 of the data processing apparatus 14 and the remote wireless communications module 30 utilize the same standards to ensure compatibility.

It is to be understood that the foregoing details pertaining to the data processing apparatus 14 and the components part of the communications link to the Internet 36 are presented by way of example only and not of limitation. Furthermore, it is to be understood that only those components that are pertinent to the following discussion of the presently contemplated method and system for enhancing emotional state are shown. Those having ordinary skill in the art will recognize that typical mobile communications devices include many other components that have not been mentioned, and such omissions are not understood to be limiting.

Figure 2A:
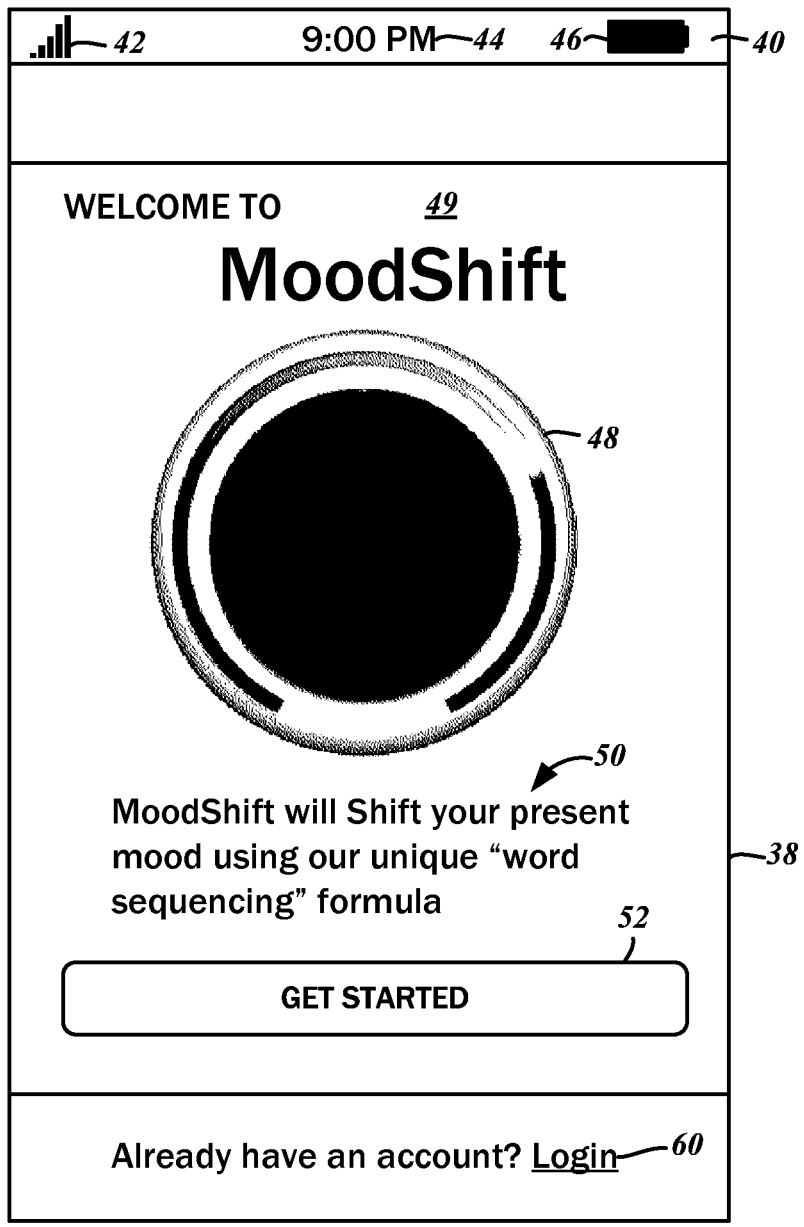
FIG. 2A is an example user interface showing an introductory screen.

As indicated above, one embodiment of the present disclosure contemplates the system and method for shifting and recharging the emotional state of the user 12 being implemented as a software application that runs on the data processing apparatus 14, and FIG. 2A and FIG. 2B are an exemplary user interface 38 thereof. The data processing apparatus 14 is understood to run an operating system that controls the aforementioned input and output devices, as well as to provide a unified user interface. One of the unified elements is a top bar 40 with a wireless communication link strength icon 42, a clock 44, and a battery power indicator icon 46. The foregoing is presented by way of example only, and other operating systems of different data processing apparatuses 14 may utilize different graphical user interfaces.

Specifically, the example screen shown in FIG. 2A is an introductory screen 49 that is displayed upon invoking the software application. Various graphics such as logos 48 may be generated on the user interface 38, along with some introductory text 50. The user 12 may select a start button 52 to continue.

Personalization of the various functions and features of the software application is contemplated. In some cases, the identity information may be stored locally on the data processing apparatus 14, but in others this data may be stored remotely. With reference again to the block diagram of FIG. 1, one of the remote systems connected to the Internet 36 is an application support system 54, on which personal account data may be stored. More particularly, there may a server computer system 56 connected to a database 58, though this is by way of example and any other implementation of the application support system 54 may be utilized. Referring back to FIG. 2A, to load the various personalization variables, a login function may be invoked via a login button 63.

Now referring to FIG. 2B, invoking the login button 63 on the introductory screen 49 shown in FIG. 2A results in a login screen 59 being generated in the user interface 38. It is also possible to return to the introductory screen 49 by activating a back button 51. Whether the personal account data is stored on the data processing apparatus 14 or on the application support system 54, one of the ways in which the account is accessed is by supplying an email address in an input box 60 therefor, and a password similarly in an input box 62 therefor. Upon the user 12 entering the email address and password, a login button 63 may be invoked to complete the account login process. If the user has forgotten the correct password, it may be recovered by selecting a password recovery link 64. This results in a password recovery screen 66 being generated in the user interface 38 as shown in FIG. 2C. The email with which the account was created can be entered in another email input box 68, and a temporary password along with instructions on resetting the password may be sent thereto upon invoking a send button 70. To cancel the password reset process, a return/login button 72 may be invoked to return to the login screen 59 shown in FIG. 2B.

However, referring additionally to the block diagram of FIG. 1, it is understood that an account established on a social networking service site 74 may also be utilized to access the personal account data. One of the most popular social networking services is Facebook, which can be accessed via a first social networking site login button 76a, while Twitter is another, and can be accessed via a second social networking site login button 76b. As will be recognized by those having ordinary skill in the art, the social network service site 74 maintains an extensive volume of user information, and can be utilized as credentials to access other services and data, including the presently contemplated application support system 54 and the personal account data stored thereon.

Figure 3:
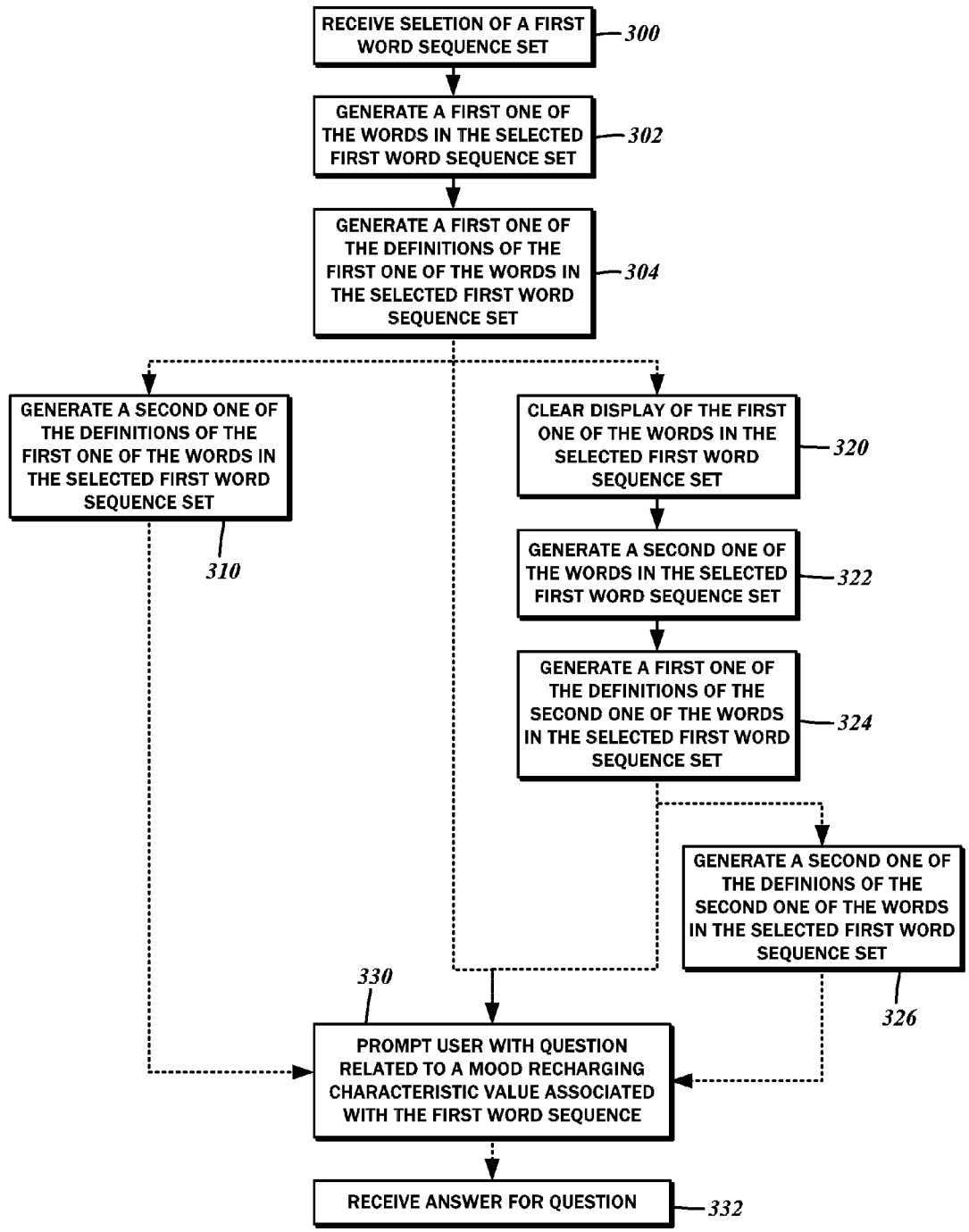
FIG. 3 is a flowchart illustrating one embodiment of a method for shifting and recharging an emotional state of a user with word sequencing.

With reference to the flowchart of FIG. 3, the method may begin with a step 300 of receiving a selection of a first word sequence set. In the embodiment of the present disclosure implemented as a software application running on the data processing apparatus 14, this selection may be received via a word sequence set selection screen 78 shown in FIG. 4. More particularly, the word sequence set selection screen 78 includes a listing 80 of available word sequence sets stored on the data processing apparatus 14 each represented as a list element 82. Each list element 82 is delineated with a word sequence set descriptor 79. The next step in the method may be initiated upon a user activation of a begin button 83.

Figure 5:
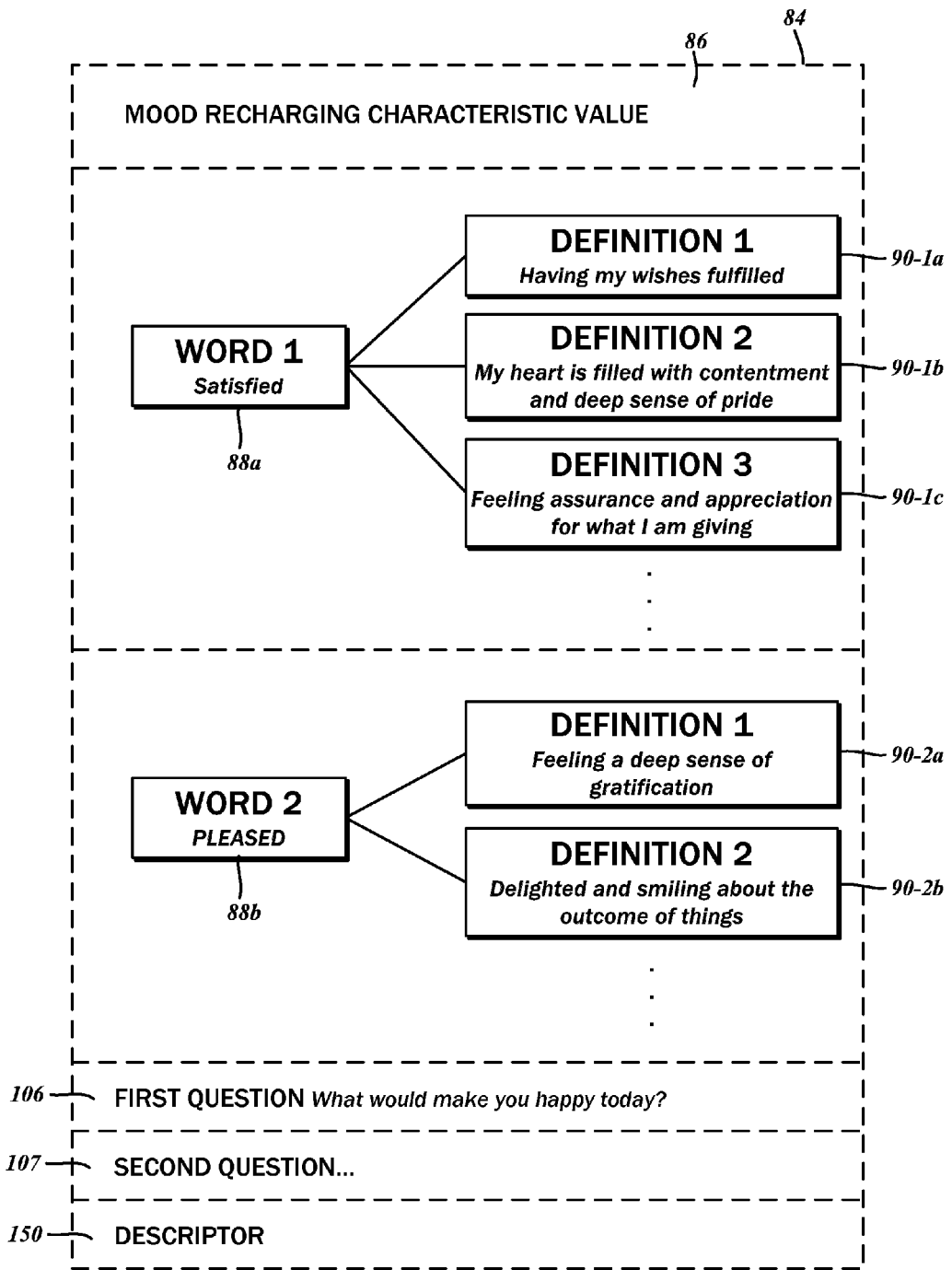
FIG. 5 is a data structure diagram of word sequence sets in accordance with one embodiment of the present disclosure.

Generally, a word sequence set is understood to be a collection of words each having one or more corresponding definitions. The data structure diagram of FIG. 5 illustrates one exemplary embodiment of a first word sequence set 84, which may be defined by a mood recharging characteristic value 86. This may be a short descriptor that briefly sets forth the mood shifting and recharging objective of the word sequence set 84, and may be utilized for the word sequence set descriptor 150 in the listing 80 discussed above. One example mood recharging characteristic value 86 may be "Happiness." The first word sequence set 84 includes multiple words 88, including a first word 88a, and a second word 88b. It will be recognized that the word sequence set 84 may include additional words 88, though in the example there are only two. The mood recharging characteristic value 86 is understood to define the overall theme or characteristic that is shared amongst the plurality of words 88.

By way of example, the first word 88a may be "Satisfied" and the second word 88b may be "Pleased," both of which are related to the "Happiness" mood recharging characteristic value 86. There may be additional word sequence sets 84 with a corresponding mood recharging characteristic value 86 such as "Confidence" and "Energy," that are understood to include words 88 that fit the respective themes. Each word in the word sequence set 84, in turn, has at least one corresponding definition 90. For example, the first word 88a may have a first definition 90-1a with a value of "having my wishes fulfilled," a second definition 90-1b with a value of "my heart is filled with contentment and a deep sense of pride," and a third definition 90-1c with a value of "feeling assurance and appreciation for what I am giving." For the second word 88b, there may be a first definition 90-2a with a value of "feeling a deep sense of gratification," and a second definition 90-2b with a value of "delighted and smiling about the outcome of things." As with the variable number of words 88 in the word sequence set 84, there may be a variable number of definitions 90 for each word 88.

The definition 90 for a given word 88 is not a "definition" in the strictest sense, but rather, a related concept that could be associated with the word 88. Along these lines, although the word 88 is a single, standalone word in the illustrated example, it may also be a short phrase or multiple words. The combination of the word 88 with the definitions 90 is contemplated to stimulate emotional activity relating to the subjects thereof, and influence thought in a manner that recharges the emotions of the user 12. Therefore, possible envisioned uses for the application include boosting confidence of the user 12 before a romantic date, a business meeting, or an exam and providing encouragement before a challenging situation. Additionally, when the user 12 needs emotional recharging, including but not limited to increased energy, and inspiration or encouragement, the application can be initiated. It will be appreciated that an infinite number of the words 88 and the corresponding definitions 90 may be provided to further tailor the mood improvement objectives of the application to an ever-increasing number of users 12. The example words 88 and definitions 90 presented herein are not intended to be limiting, and any other suitable content may be utilized.

The first word sequence set 84 is understood to be stored on the data processing apparatus 14. It is also contemplated, however, that periodic updates may be made to the word sequence sets 84 and made available on the application support system 54. Accordingly, prior to proceeding to the next step in the method, the application support system 54 may be queried to determine whether any updates are available. The possible type of updates may include additions, replacements, or deletions of any one of the definitions 90, as well as additions and deletions of any one of the words 88. If any exist, those updates are downloaded applied to the locally stored copy of the word sequence set 84. In cases where the update revises one of the definitions 90, it may be so specified within the update that it is to replace the existing one with the updated one. Similarly, additional definitions 90 to a particular one of the words 88 may also be specified as adding to, rather than replacing, an existing one. Updates to the words 88 are understood to be processed in a similar manner. Those having ordinary skill in the art will appreciate several different update methodologies that may be used to implement the foregoing features.

Figure 6A:
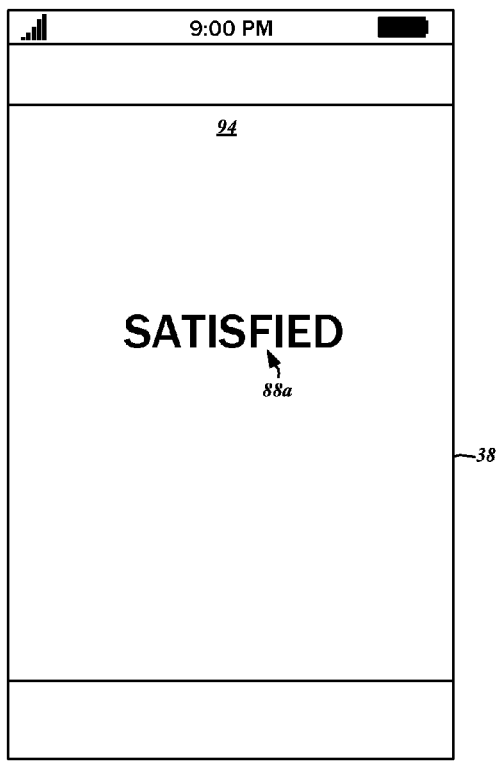
FIG. 6A-6E show an example user interface variously displaying a word display screen, a first word and definition combination display screen, and a second word and definition combination display screen, a third word and definition combination screen, and a fourth word and definition combination screen.

Returning to the flowchart of FIG. 3, the method continues with a step 302 of generating a first one of the words 88 on the display 20 of the data processing apparatus 14. An example of how this may be implemented in the application is shown in FIG. 6A, which depicts a word display screen 94. Per the foregoing example of the first word sequence set 84, the first word 88a, "Satisfied" is generated on the word display screen 94. The first word 88a is generated with a first predetermined typeface, which may be defined by either a typeface size, typeface style, or typeface enhancement such as underline, bold, italic, and so forth. Although the example shows the first word 88a being generated on the word display screen 94, the order of displaying the words 88 may be randomized, and may begin with any one of the other words in the word sequence set 84. Additionally, various transition effects involving the introduction of the first word 88a on to the word display screen 94 are possible.

As indicated above, the step 302 can be initiated based upon user input from the word sequence set selection screen 78, and in particular by, invoking the begin button 83 generated thereon. However, it is also contemplated that the step 302 can be initiated by other modalities not reliant on input from the user 12. In one embodiment, it is possible to set a time and/or date notification within the application, such that when the actual time and/or date matches that of the set notification, the application starts and proceeds to the step 302 of generating the first one of the words. This may be particularly useful for those users 12 that are preparing for a business meeting or an exam that is at a set time, and the notification is set to a time or date before that scheduled event. As such, the user 12 can be automatically notified. Another embodiment contemplates a similar initiation modality, but utilizes an on-board GPS (global positioning system) receiver 27 instead. It will be recognized by those having ordinary skill in the art that the GPS receiver 27 reports the actual coordinates of the location in which the data processing apparatus 14 is disposed. Thus, the application may be set to initiate the step 302 when the reported coordinates are proximal to that of a predefined location. This may also be referred to as a geographic notification. For example, the predefined location may be set to a public venue in which the user 12 is scheduled to speak. When the user 12 approaches that venue, positive emotional encouragement may be provided to help overcome fears of public speaking via the contemplated mood shifting and recharging methods implemented in the application. As utilized herein, the term notification may refer to any modality by which the user 12 is informed of a triggering condition, including push notifications, alarms, alerts, and any other suitable modalities available through the data processing apparatus 14. Along these lines, unique tones, sounds, or other audio may also be generated concurrently with the notifications.

Figure 6B:
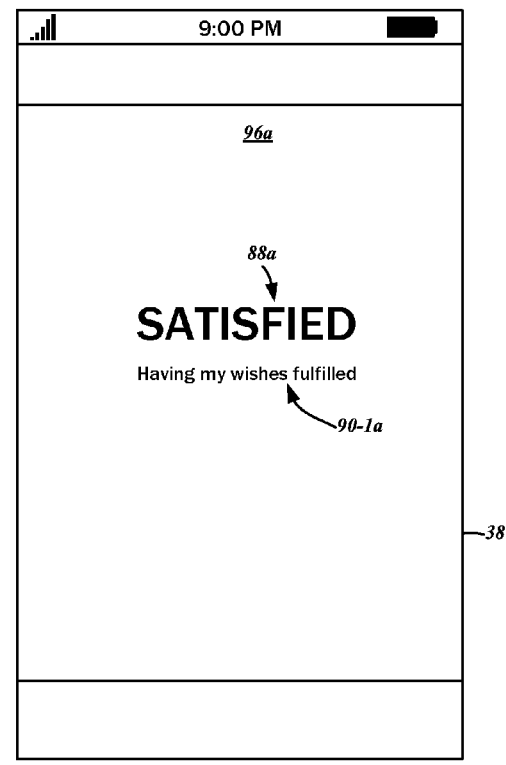

Next, the method proceeds to a step 304 of generating on the display a first one of the corresponding definitions 90 for the selected or displayed word in step 302, e.g., the first word 88a. In accordance with one embodiment of the present disclosure, this occurs in a first word and definition combination display screen 96a as shown in FIG. 6B, and the display of the first word 88a thereon is maintained. In other words, the first definition 90-1a is generated on the display 20 while the first word 88a remains generated on the same. The particular definition 90 that is shown in conjunction with the first word 88a may be randomized, and any other definition 90 corresponding to the first word 88a may be generated instead. The display of the definition 90 is contemplated to be with a second predetermined typeface that has its specific typeface size, typeface style, or typeface enhancement. Any one of these characteristics may be varied from that of the first predetermined typeface mentioned above in relation to the display of the word 88. In the illustrated example, the definition 90 is generated with a smaller typeface size than that of the corresponding word 88. However, this is by way of example only and not of limitation, and any other suitable visual effects may be made, or may be kept the same, depending on the embodiment.

Figure 7:
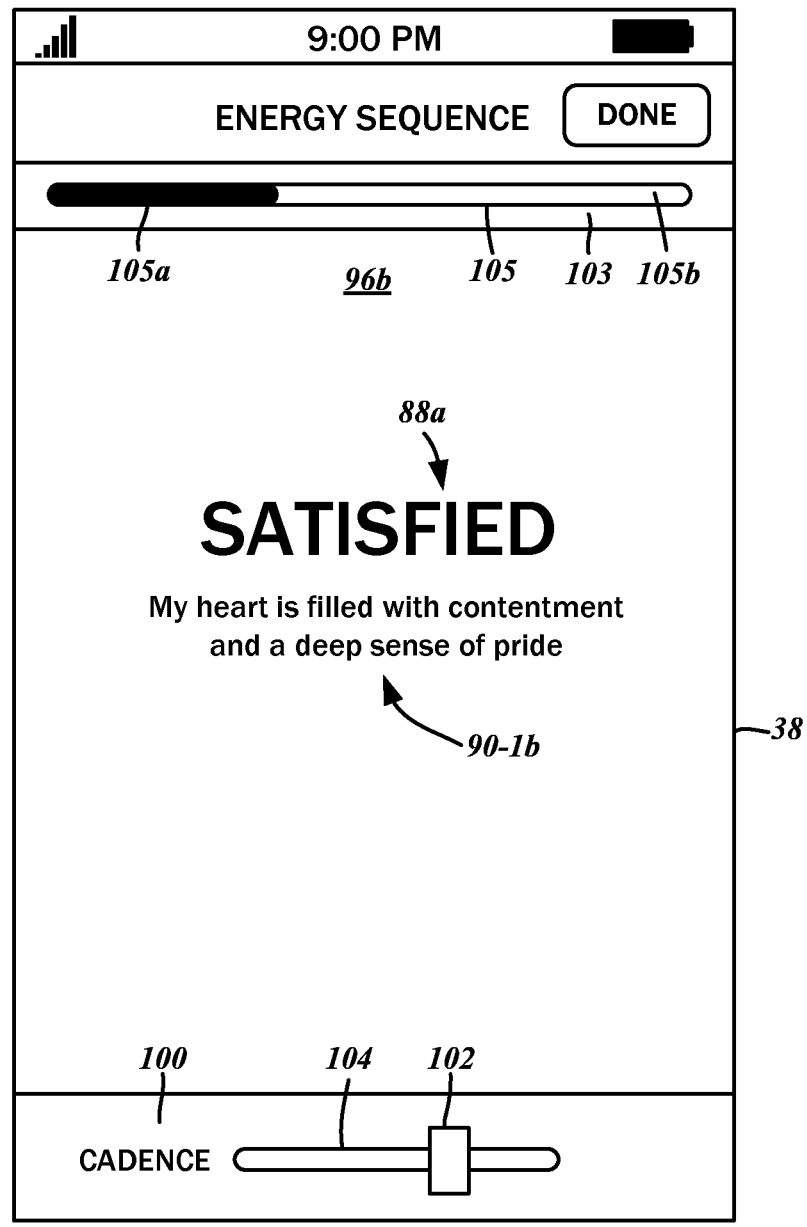
FIG. 7 is an example user interface showing the word and definition combination display screen with a cadence change overlay and a word sequence overlay.

The first definition 90-1a remains displayed for a time duration that corresponds to a predefined cadence rate value. Preferably, though optionally, the time duration is understood to be approximately five seconds, though it can be as short as three seconds. The upper limit of the time duration is understood to be ten seconds, though this is by way of example only. Any other upper limit may be substituted without departing from the scope of the present disclosure. The cadence rate value, and hence the time duration, can be modified by the user. As best shown in FIG. 7, a cadence change overlay 100 is generated in response to any touch input while either word display screen 94 or the word and definition combination display screen 96 is being presented in the user interface 38. More particularly, the cadence change overlay 100 includes a sliding button 102 that can be moved along a cadence bar 104. Depending on the specifics of the implementation, the far right position of the sliding button 102 along the cadence bar 104 may represent the fastest cadence, i.e., the lowest delay (three seconds), while the far left position of the sliding button along the cadence bar 104 may represent the slowest cadence, i.e., the highest delay (ten seconds). Notwithstanding the foregoing example, other user interface elements through which variables can set may be substituted.

Another feature that is invoked upon providing a touch input while the word display screen 94 or the word and definition combination display screen 96 is being presented on the user interface 38 is a progress overlay 103 including a progress bar 105. Although only a single word-definition shift and recharge sequence has been illustrated above, according to some embodiments, a complete shift and recharge sequence may be comprised of multiple words 88 and multiple definitions 90 being presented to the user 12. In this regard, the progress bar 105 is understood to record the progress of a started shift and recharge sequence and present a visual representation thereof having a completed portion 105a and an uncompleted portion 105b that has a different appearance than the completed portion 105a. Preferably, the progress through a shift and recharge sequence is not recorded from one instance of the application to another, but other embodiments do contemplate its possibility. Furthermore, the user 12 is expected to progress through the shift and recharge sequence from start to finish without skipping, and so the progress bar 105 may not accept any user input that shifts the order or timing of the word display screen 94 and/or the word and definition combination display screen 96. There are alternative embodiments, however, where such shifts are possible.

Figure 6C:
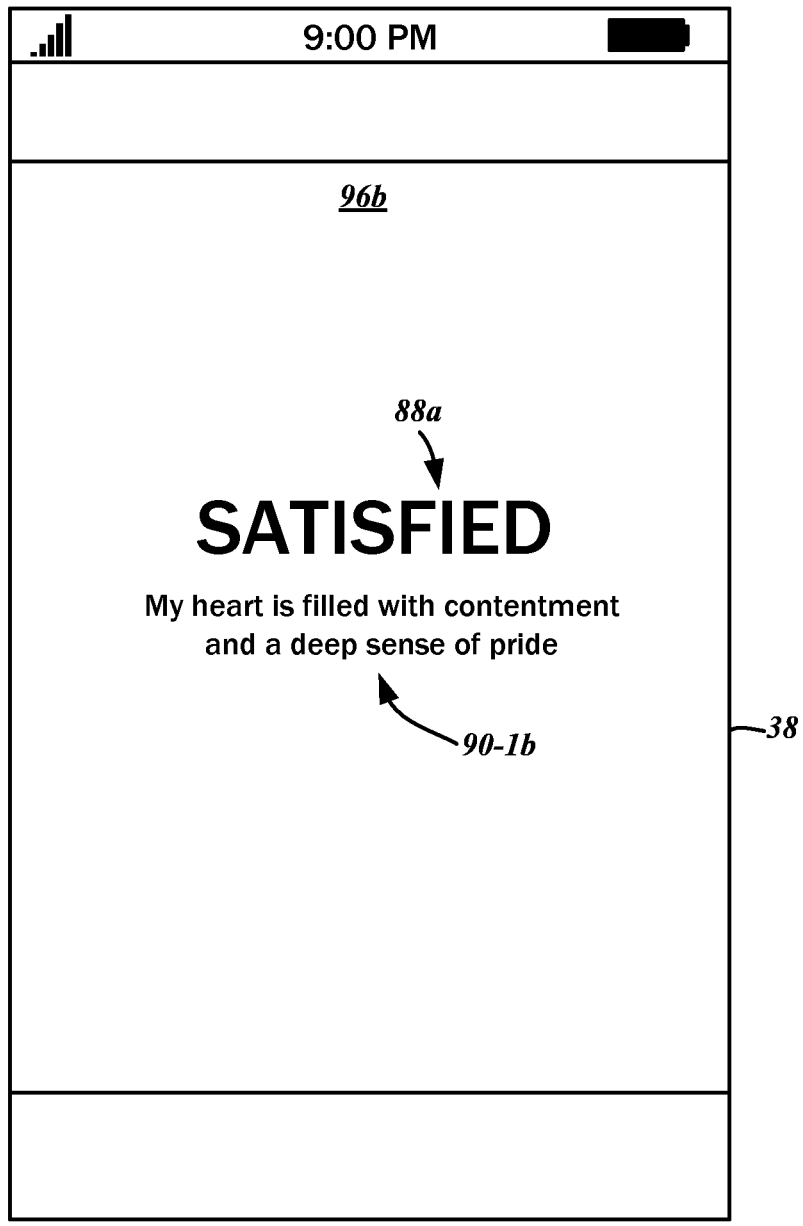

Following the step 304 discussed above, the execution of the method may diverge to different branch steps. One of these is a step 310 of generating a second one of the definitions, e.g., the second definition 90-1b for the first word 88a, on the display 20. An example is shown in FIG. 6C, which shows the user interface 38 displaying a second word and definition combination display screen 96b. Like the first definition 90-1a discussed above, the display of the second definition 90-1b is contemplated to be with the second predetermined typeface, and remains displayed for the same time duration. Prior to displaying the second definition 90-1b, the first definition 90-1a is cleared from the second word and definition combination display screen 96b. As indicated above, each word 88 may have a variable number of definitions 90. In accordance with one embodiment of the present disclosure, three definitions 90 may be presented for each word 88, though this may be varied.

Figure 6D:
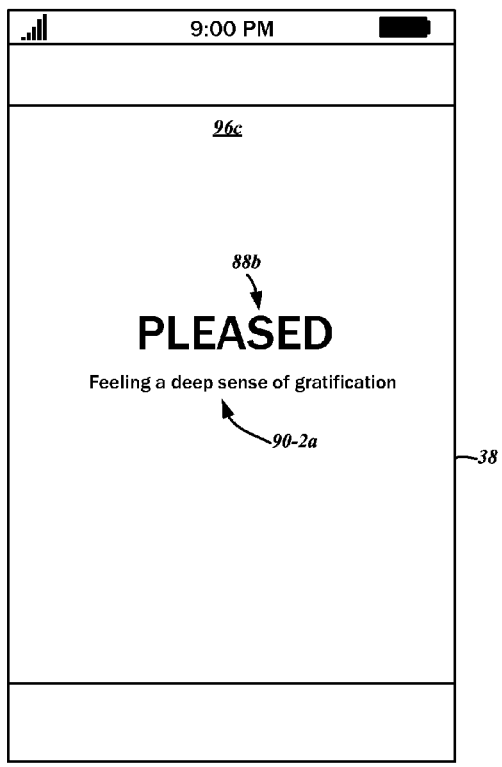

After presenting the selected definitions 90 for the first word 88a, instead of presenting another definition for the same word, the method may proceed to generate a different, second word 88b and the corresponding definitions therefor. More particularly, this may involve a step 320 of clearing the display of the first word 88a. With reference to a third example word and definition combination display screen 96c shown in FIG. 6D, this clearing step may be followed by a step 322 of generating a second one of the words 88, i.e., the second word 88b, on the display 20 of the data processing apparatus 14. Continuing with the foregoing example, the second word 88b is "Pleased." Again, the second word 88b is generated with the first predetermined typeface.

Thereafter, the method may continue with a step 324 of generating a first one of the definitions 90 of the second word 88b, that is, the first definition 90-2a. This, by way of example, is "feeling a deep sense of gratification" for the second word 88b "Pleased." Like the other presentations of the definition 90, the first definition 90-2a is generated in the second predetermined typeface, and only for a limited period as governed by the time duration corresponding to the cadence rate value.

Figure 6E:
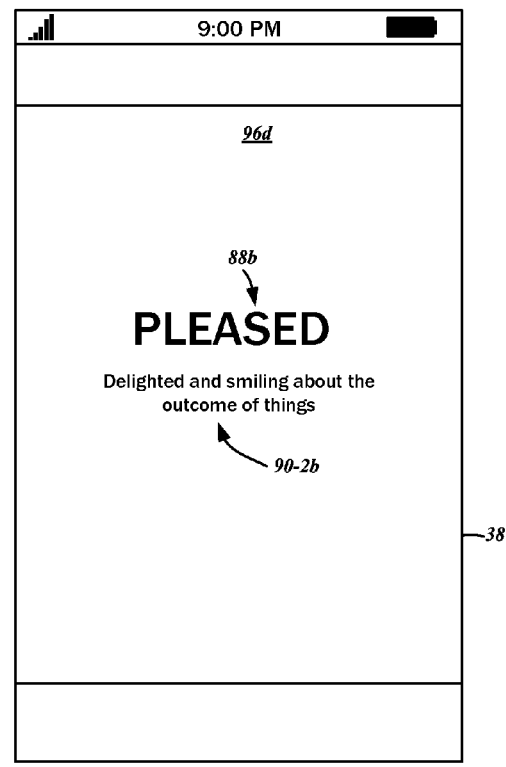

Once the time duration for displaying the first definition 90-2a has elapsed, the method may proceed to a step 326 of generating a second definition 90-2b for the second word 88b. This is understood to be generated on a fourth word and definition combination display screen 96d shown in FIG. 6E. According to the illustrated example, the second definition 90-2b is "delighted and smiling about the outcome of things." Similar to the first definition 90-2a, the 90-2b is generated with the second predetermined typeface.

Different words 88 and corresponding definitions 90 may thus be generated on the display 20 in sequence. In one embodiment of the present disclosure, the number of words 88 generated and the number of corresponding definitions 90 generated is predefined, for example, six words, three definitions each, though which of the specific words 88 and definitions 90 are to be presented may be randomized at the time of running the application. The above-described steps in the method for shifting and recharging the emotional state of the user 12 is repeated for those additional words 88 and definitions 90 of the selected word sequence set 84.

Figure 8A:
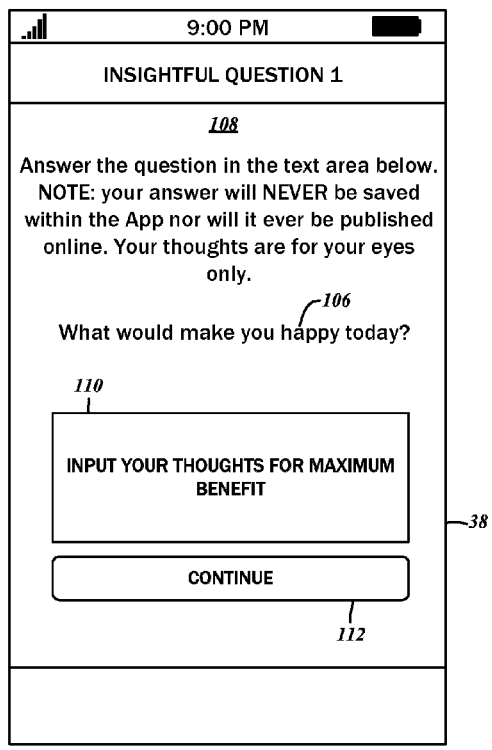
FIG. 8A-8B shows an example user interface with a question display screen and a confirmation screen.

Following the completion of the word-definition display sequence, whether following step 304, step 310, or step 326, the method may proceed to a step 330 of prompting the user 12 with a question related to the mood recharging characteristic value 86 of the first word sequence set 84. Referring back to the data structure diagram of FIG. 5, the word sequence set 84 also includes a question 106, which may ask, for example "What would make you happy today?" With reference to the example user interface 38 shown in FIG. 8A, the question 106 may be presented in a question display screen 108. Displayed within the question display screen 108 is the question 106, as well as a text input box 110.

The purpose of the question 106 is envisioned to sustain the shift and recharge of the mood of the user 12 following the mostly passive reception of the word-definition sequence in previous steps. The associations created as a result of the generated sequence of the word 88 and the definition 90 is further reinforced by the user 12 with question 106, creating a personal link, association, or connection, therefore creating sustainability of the mood shift and recharge. Due to the open-ended, probing nature of the question 106, they may also be referred to as insightful questions. Although a single question 106 is shown associated with the word sequence set 84, there may be additional ones, and may be selected at random in relation to the step 330. In addition, there may be a second question 107 that can be presented to the user 12 independent of the step 330, to further advance the sustainability of the mood shift and recharge. This question may not necessarily relate to the specific word 88 that has been presented, but relate overall to the word sequence set 84. The aforementioned procedures of updating the various components of the word sequence set 84 are understood to be applicable to the question 106 as well.

Figure 8B:
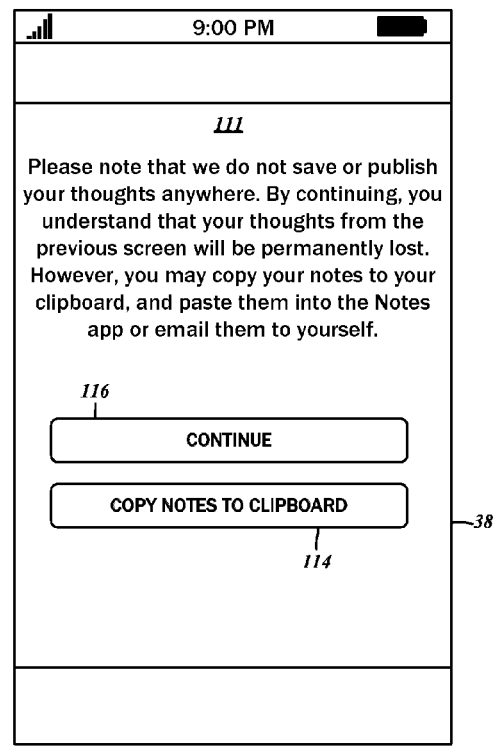

The method continues with an optional step 332 of receiving a user-supplied answer to the question 106. The answer is provided by the user 12 via the text input box 110, and upon completion, the next step in the process may be invoked by pressing a continue button 112. The answer to the question 106 is not retained in various embodiments, though it is possible to do so if desired or warranted. With reference to FIG. 8B, the user 12 is warned of the fact that the answer to the question 106 is not retained or otherwise saved in a confirmation screen 111. However, if desired for journal keeping purposes, the answer may be copied to the system clipboard by invoking a copy button 114. Otherwise, the next step in the application is invoked by a continue button 116.

Figure 9A:
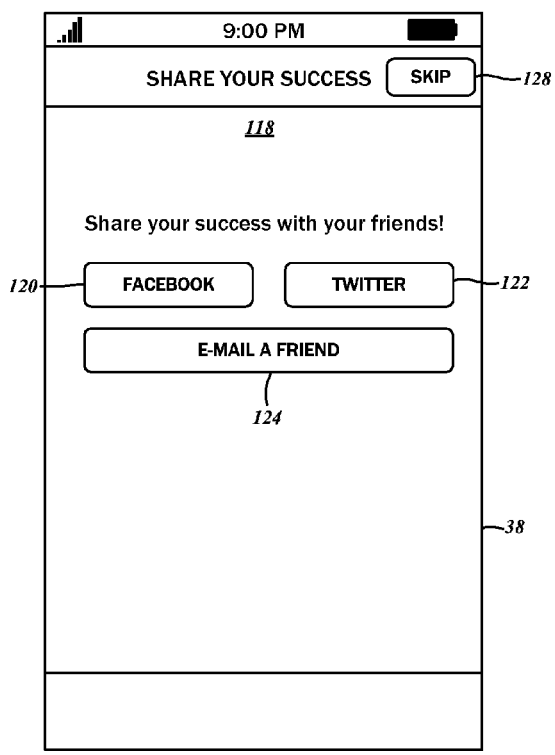
FIG. 9A-9B shows an example user interface with a sharing screen, and an input screen.
Figure 9B:
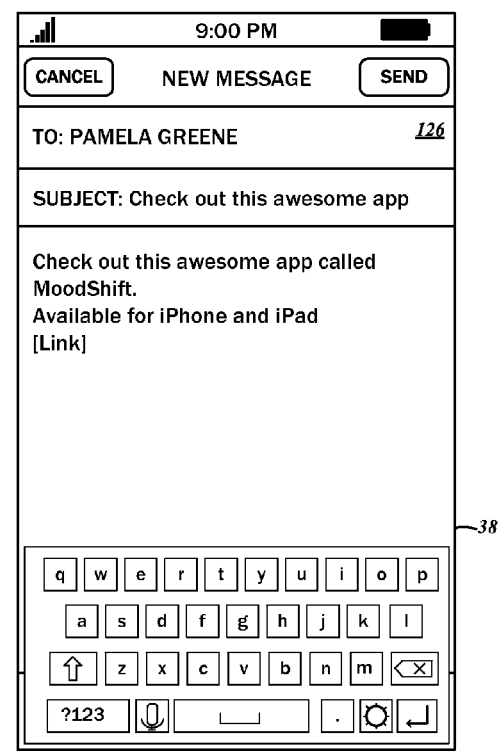

One embodiment contemplates a sharing functionality by which the user 12 can announce to friends and acquaintances on various social networking sites 74 that a word sequence set has been completed. As best shown in the exemplary user interface 38 shown in FIG. 9, there is a sharing screen 118 with a first button 120 to invoke sharing functions in relation to a first social networking site, a second button 122 to invoke sharing functions in relation a second social networking site, and a third button 124 to invoke e-mail sharing functions. Upon selecting one of these first, second or third buttons 120, 122, 124, a corresponding input screen particular to that sharing feature may be generated in the user interface 38 to accept input or confirm a default message. Those having ordinary skill in the art will recognize the numerous possible implementations of the input screen.

Figure 10:
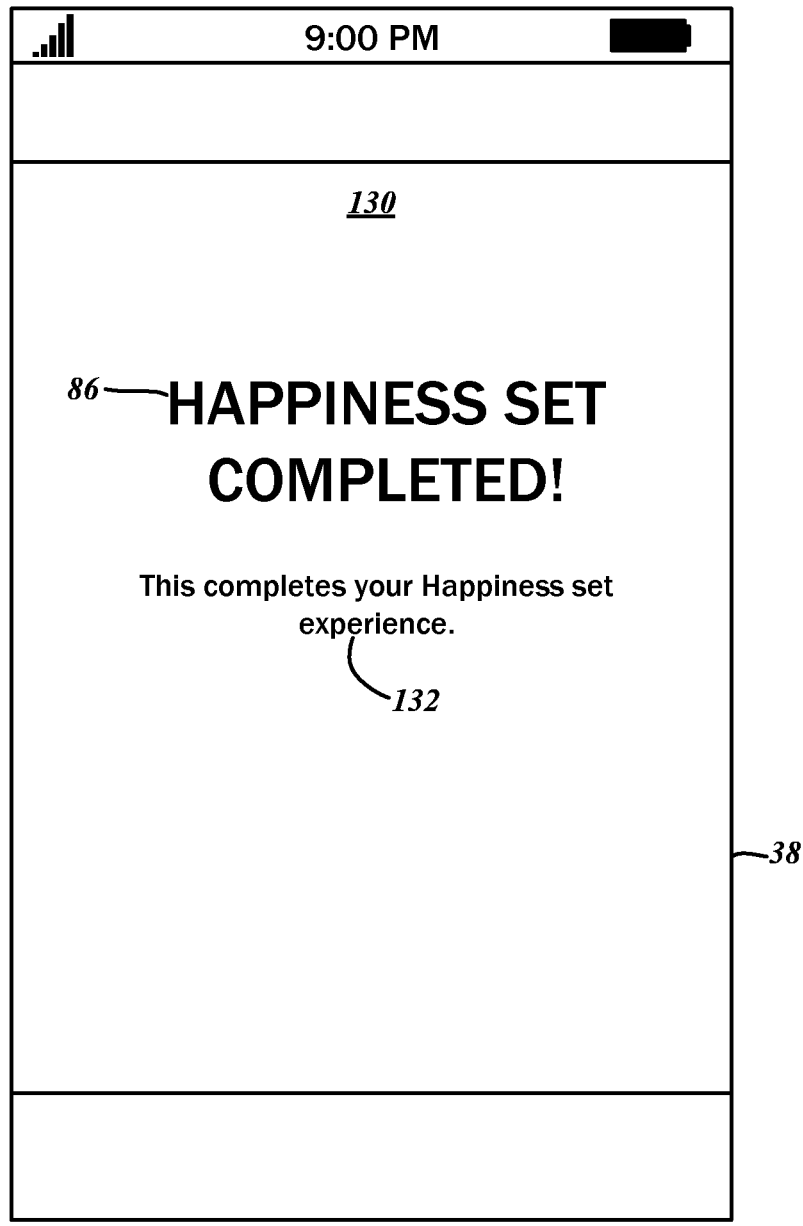
FIG. 10 shows an example user interface with a final confirmation screen.

The sharing step may be skipped, and this option is possible by invoking a skip button 128. Whether the completion message is shared or not, however, execution proceeds to a final confirmation screen 130 shown in FIG. 10. Therein the mood recharging characteristic value 86 is mentioned to identify the particular word sequence set 84 that the user 12 has completed. Additionally, there is a congratulatory message 132.

Figure 4:
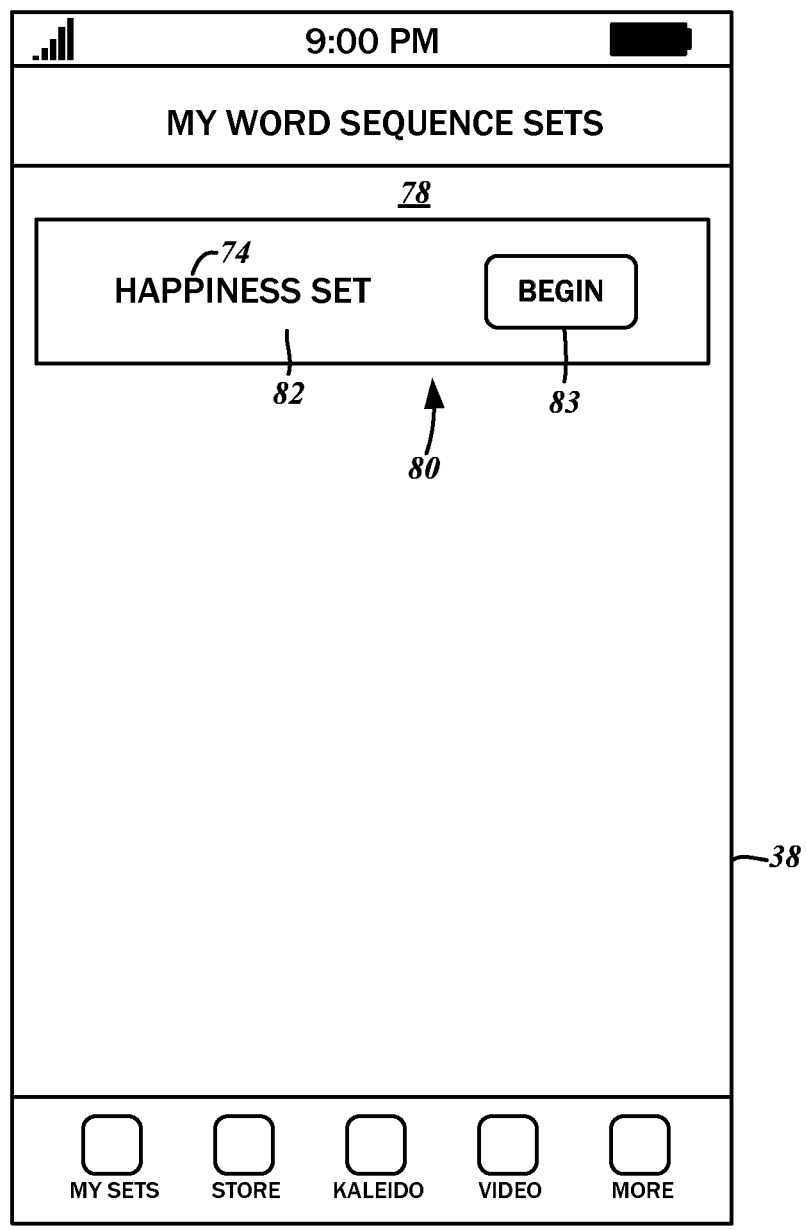
FIG. 4 is an example user interface showing a word sequence set selection screen.

Referring back to the word sequence set selection screen 78 of FIG. 4, it is understood that the listing 80 includes the word sequence sets 84 stored on the data processing apparatus 14. According to various embodiments of the present disclosure, it is possible to purchase additional word sequence sets 84 provided by the application support system 54. As shown in the block diagram of FIG. 1, the provider of the data processing apparatus 14 typically maintains an application distribution system 134 with a catalog of available software programs for download. Some of the programs are sold, so there may be a payment processing system 136. In order to purchase additional word sequence sets 84, the request may be first routed through the third-party application distribution system 134. The payment may be remitted from the data processing apparatus 14 to the payment processing system 136, and upon successful payment/authorization, directs the application server system 54 to transmit the purchased word sequence set 84. A variety of secure methods for processing payment are known in the art, and any one may be substituted without departing from the scope of the present disclosure.

Figure 11:
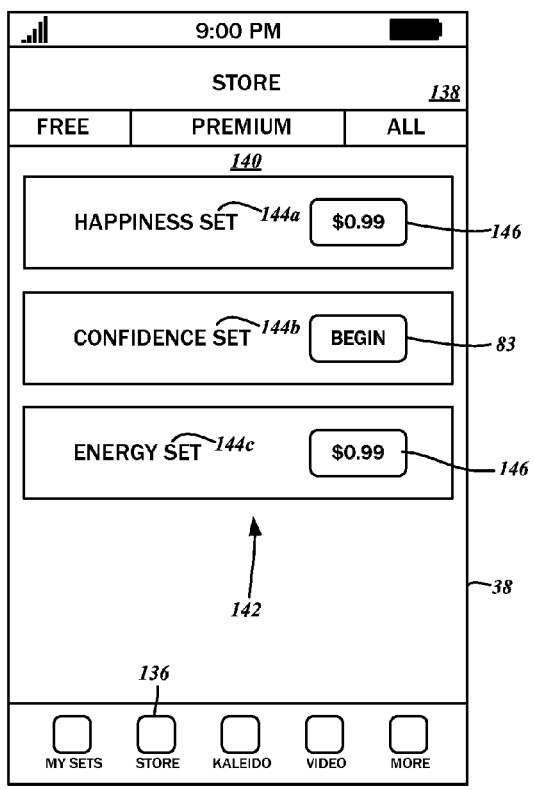
FIG. 11 shows an example user interface with a purchase or store screen.

From the word sequence set selection screen 78, a store icon 136 may be invoked to show the available word sequence sets 84 available for purchase. More particularly, as shown in FIG. 11 a purchasing or store screen 138 is generated in the user interface 38, and likewise includes another listing 140 of descriptors 144 corresponding to the mood recharging characteristic values 86 of the respective word sequence sets 84. In the illustrated example, there is a word sequence set 84 for "Confidence" per the descriptor 144a, for "Happiness" per the descriptor 144b, and for "Energy" per the descriptor 144c. Those word sequence sets 84 already purchased and stored on the data processing apparatus are also included in the listing 140, distinguished by the begin button 83. Those not yet purchased are set apart with a price tag button 146 that shows the offer price, and the invocation of which is operative to begin the purchase process.

Figure 12:
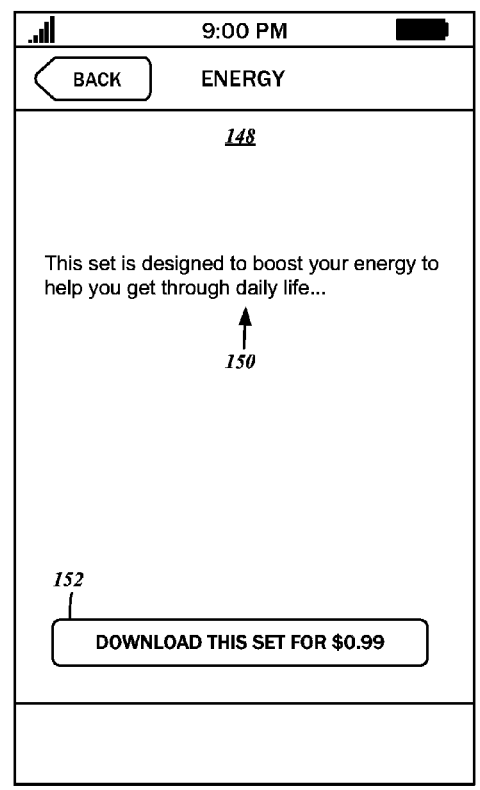
FIG. 12 shows an example user interface with a word sequence set description screen.

A more detailed description of a given word sequence set 84 may be presented in a word sequence set description screen 148 as shown in FIG. 12. Referring to the data structure diagram of FIG. 5, each word sequence set 84 is understood to include a descriptor 150 that provides an overview of the goals thereof. While the word sequence set 84 may be purchased directly from the listing 140 via the corresponding price tag button 146, purchasing from the word sequence set description screen 148 is also possible by selecting a purchase button 152. Subsequent standard interactivity common to in-application purchases conducted through the application distribution system 134 is contemplated, including various confirmation dialog boxes, and download progress meters.

The particulars shown herein are by way of example and for purposes of illustrative discussion of the embodiments of the present disclosure only and are presented in the cause of providing what is believed to be the most useful and readily understood description of the principles and conceptual aspects. In this regard, no attempt is made to show details of the present invention with more particularity than is necessary, the description taken with the drawings making apparent to those skilled in the art how the several forms of the present invention may be embodied in practice.

What is claimed is:

1. A method for shifting and recharging an emotional state of a user with word sequencing presented on a data processing apparatus with a display and an input, the method comprising the steps of:

receiving, from the user through the input of the data processing apparatus, a selection of a first word sequence set defined by a mood recharging characteristic value, the first word sequence set including a plurality of words each with at least one corresponding definition;

generating on the display with a first predefined typeface a first one of the plurality of words in the selected first word sequence set;

generating on the display with a second predefined typeface, while the first one of the plurality of words remains generated on the display, a first one of the at least one corresponding definition of the first one of the plurality of words in the selected first word sequence set for a time duration corresponding to a predefined cadence rate value; and prompting the user with a question related to the mood recharging characteristic value and associated with the first word sequence set.

2. The method of claim 1, further comprising:

receiving on the data processing apparatus through the input a user-supplied answer to the question.

3. The method of claim 1, wherein prior to prompting the user with the question, the method includes:

generating on the display with the second predefined typeface, while the first one of the plurality of words remains generated on the display, a second one of the at least one corresponding definition of the first one of the plurality of words in the selected first word sequence set for the time duration.

4. The method of claim 1, wherein prior to prompting the user with the question, the method includes:
clearing the display of the first one of the plurality of words in the selected first word sequence set;
generating on the display with the first predefined typeface a second one of the plurality of words in the selected first word sequence set; and
generating on the display with the second predefined typeface, while the second one of the plurality of words remains generated on the display, a first one of the at least one corresponding definition of the second one of the plurality of words in the selected first word sequence set for the time duration.

5. The method of claim 4, wherein prior to prompting the user with the question, the method includes:
generating on the display with the second predefined typeface, while the second one of the plurality of words remains generated on the display, a second one of the at least one corresponding definition of the second one of the plurality of words in the selected first word sequence set for the time duration.

6. The method of claim 1, wherein the time duration is within a range of three to ten seconds.

7. The method of claim 1, further comprising:
receiving through the input a modification to the predetermined cadence rate value; and
updating the time duration according to the modification to the predetermined cadence rate value.

8. The method of claim 1, wherein the first predefined typeface has a first size and the second predefined typeface has a second size different from the first size.

9. The method of claim 1, wherein the first predefined typeface has a first visual style and the second predefined typeface has a second visual style different from the first visual style.

10. The method of claim 1, wherein the first one of the plurality of words in the selected first word sequence set is generated on the display of the data processing apparatus in response to a preset time notification.

11. The method of claim 1, wherein the first one of the plurality of words in the selected first word sequence set is generated on the display of the data processing apparatus in response to a geographic notification based upon a location value detected by the data processing apparatus being within a predefined distance of a trigger location.

12. The method of claim 1, wherein the first word sequence set is stored on the data processing apparatus.

13. The method of claim 12, further comprising:
querying a remote server for updates to the first word sequence set; and
receiving the queried updates to the first word sequence set on the data processing apparatus.

14. The method of claim 13, wherein the updates include at least one update definition for a one of the words in the first word sequence set.

15. The method of claim 14, further comprising:
overwriting a selected one of the definitions of the one of the words in the first word sequence set stored on the data processing apparatus with the corresponding received update definition.

16. The method of claim 14, further comprising:
adding the received update definition to the one of the words in the first word sequence set stored on the data processing apparatus.

17. The method of claim 13, wherein the updates include a new word and at least one corresponding new definition therefor.

18. The method of claim 17, further comprising:
adding the received new word and the at least one new definition to the first word sequence set stored on the data processing apparatus.

19. The method of claim 1, further comprising:
transmitting to a remote server, a word sequence set purchase request including a payment authorization;
receiving a second word sequence set from the remote server; and
storing the second word sequence on the data processing apparatus.

20. The method of claim 1, wherein the data processing apparatus is a smart phone.

21. A non-transitory computer readable medium having computer-executable instructions for performing a method for shifting and recharging an emotional state of a user with word sequencing presented on a computer with a display and an input, the method comprising the steps of:
receiving, from the user through the input of the computer, a selection of a first word sequence set defined by a mood recharging characteristic value, the first word sequence set including a plurality of words each with at least one corresponding definition;
generating on the display with a first predefined typeface a first one of the plurality of words in the selected first word sequence set;
generating on the display with a second predefined typeface, while the first one of the plurality of words remains generated on the display, a first one of the at least one corresponding definition of the first one of the plurality of words in the selected first word sequence set for a time duration corresponding to a predefined cadence rate value;
prompting the user with a question related to the mood recharging characteristic value and associated with the first word sequence set; and
receiving on the data processing apparatus through the input a user-supplied answer to the question.

* * * * *